US00PP10337P

United States Patent [19]

Sorensen

[11] Patent Number: Plant 10,337

[45] Date of Patent: Apr. 21, 1998

[54] OSTEOSPERMUM PLANT NAMED 'CAPE DAISY LUSAKA'

[75] Inventor: Carl Aksel Kragh Sorensen, Åbyhoj, Denmark

[73] Assignee: Paul Ecke Ranch, Encinitas, Calif.

[21] Appl. No.: 695,342

[22] Filed: Aug. 9, 1996

[51] Int. Cl.[6] ..... A01H 5/00

[52] U.S. Cl. ..... Plt./68.1

[58] Field of Search ..... Plt./68.1

[56] References Cited

PUBLICATIONS

UPOV–ROM Plant Variety Database 'Cape Daisy Lusaka' PBR OST 00022, 1994.

*Primary Examiner*—Howard J. Locker
*Assistant Examiner*—Melissa L. Kimball
*Attorney, Agent, or Firm*—Arnold, White & Durkee

[57] ABSTRACT

A new and distinct cultivar of Osteospermum named 'Cape Daisy Lusaka', particularly characterized by its upright spreading growth habit with excellent purple flower color, early season flowering and medium green foliage, and suitability to 6 inch pots, nursery containers and 8 and 10 inch hanging basket cultures.

1 Drawing Sheet

BACKGROUND OF THE INVENTION

The present invention relates to a new and distinct cultivar of plant known as Osteospermum. The new cultivar is known by the cultivar name 'Cape Daisy Lusaka', and was developed by the inventor Mr. Carl Aksel Kragh Sorensen in Aarhus, Denmark in 1994 by crossing the cultivars 'Cape Daisy Pink Fantasy' and 'Cape Daisy Zimba'. 'Cape Daisy Pink Fantasy' is unpatented and 'Cape Daisy Zimba' is described and illustrated in co-pending U.S. Plant Pat. application No. 08/695,341.

Asexual reproduction by terminal (stem tip) cuttings taken by me or under my supervision at Peterminde Greenhouse in Aarhus, Denmark, has shown that the unique features of this new Osteospermum are stabilized and are reproduced true to type in successive propagations.

The following characteristics distinguish the new Osteospermum from both its parent varieties and other cultivars of this general type known and used in the floriculture industry:

1. A unique purple flower color.
2. An upright, spreading growth habit.
3. Early flower response.
4. Well suited for 6" pots, nursery containers, and hanging baskets.

'Cape Daisy Lusaka' is similar to 'Tonga', an patented variety, and the variety 'Sunny Lady', the plant described and illustrated in co-pending U.S. Plant Pat. application, No. 08/698, 336. The growth habit of 'Cape Daisy Lusaka' is more upright, flower petioles are longer, and plant structure is more open than either 'Tonga' or 'Sunny Lady'. 'Cape Daisy Lusaka' ray florets are longer and distinctly two-tone purple as compared to 'Sunny Lady'.

Chart A compares 'Cape Daisy Lusaka' with 'Sunny Lady' which is the closest plant to the inventor's knowledge. 'Sunny Lady' is the plant described and illustrated in co-pending U.S. Plant application, No. 08/698,336. Chart A describes three plants grown together in a hanging basket. t.20

Immature flowers of 'Lusaka' are light purple near R.H.S. 75B on opening and change to a medium purple at maturity. Flowers of 'Sunny Lady' are a medium purple on opening and darken only slightly at maturity.

DESCRIPTION OF PHOTOGRAPH

The accompanying colored photograph is a top perspective view of the new cultivar, showing color as true as it is reasonably possible to obtain in a colored reproduction of this type.

DESCRIPTION OF THE PLANT

The following is a detailed description of my new Osteospermum cultivar based on plants grown under commercial practice in Encinitas, Calif. Three rooted cuttings were transplanted into 26 cm (10 inch) hanging baskets on Dec. 11, 1995. Plants were pinched on Jan. 2, 1996, and received plant growth regulator on January 16 and 31. The values, measurements and observations noted below were taken from plants in bloom on Feb. 29, 1996 and continued to flower past April 1996.

On Apr. 8 ,1996, I observed a plant in a 26 cm hanging basket 47 cm tall. This basket had three branched plants with an overall height of 59 cm and an overall width of 61 cm. Each plant had 5 strong branches, originating from within 1.5 cm of the soil line, for a total of 15 branches. Each branch was approximately 22 cm long terminating in a flower. At observation, there were 34 flowers open and 70 flower buds in various stages of development. Three secondary shoots subtend the terminal flower from the top 3 nodes on the primary shoot. These secondary shoots were 22 to 29 cm in length and terminated in a flower.

Color references are made to The Royal Horticultural Society Colour Chart (R.H.S.), except where general terms of ordinary dictionary significance are used.

The Plant

Origin: Seedling from cross pollination.

Parentage: Cross between Seed Parent 'Cape Daisy Pink Fantasy' and Pollen Parent 'Cape Daisy Zimba'.

Classification:

*Botanical.*—*Osteospermum ecklonis.*

*Common name.*—Osteospermum.

*Cultivar name.*—'Cape Daisy Lusaka'.

Asexual reproduction:

A. *Cutting type.*—Vegetative shoot tip with stems approximately 3 cm long and developing to 4–5 cm after 28 days in propagation.

B. *Time to initiate roots.*—8–10 days at 20° C.; nicely developed root mass in 21–28 days.

C. *Rooting habit.*—Numerous, fibrous adventitious roots from the stem base.

D. *Growth retardant application.*—Standard growth retardant application for 'Cape Daisy Lusaka' includes 1–2 applications of Daminozide/Butanedioic acid mono (2.2 dimethylhydrazide) at a rate of 2,500 ppm. Applications are made as foliar sprays. Growth retarding chemicals generally reduce plant height by ⅓.

Plant description:

A. *Form.*—Symmetrical, upright medium-tall perennial shrub, with good branching characteristics after pinching, giving the plant a full appearance.

B. *Growth habit.*—Vigorous, upright habit, producing approximately 12 leaves per stem and terminating in flowers. After the initial flower is formed, typically three sub-ordinate shoots develop from the nodes of the uppermost leaves producing additional flowering shoots. This process is continuous so long as night temperatures remain lower than 16° C.

*Foliage description.*—1. Leaf shape: Obovate with acuminate tip and attenuate leaf base. 2. Leaf blade size: Mature leaves 9.5 cm long and 2.5 cm wide. 3. Petiole length: Approximately 3 cm in length. 4. Leaf Margin: Slightly sinuate with 2–3 pointed lobes on either side of the leaf blade. 5. Leaf texture: Slightly undulant and twisted at the tip. (i) Upper surface: Slightly pubescent with short, white trichomes evenly distributed throughout the leaf surface. (ii) Under surface: Glabrous. 6. Leaf color: Green. (i) Upper surface: Near R.H.S. 147A. (ii) Under surface: Near R.H.S. 147 A. 7. Venation: Palmately branched with a predominate light green mid-rib on the upper surface. One prominent mid-vein is slightly raised on the lower surface. 8. Foliage fragrance: Characteristic Osteospermum plant fragrance, particularly notable when foliage is wet.

Inflorescence description: Daisy type composite flower with disk and ray florets that close at night and open in the morning. The ligulate petal of the ray floret subtends the pistil. The disk florets contain male flower parts. Florets on the flower heads are imperfect with pistillate ray florets and staminate disk florets.

A. *Flowering habits.*—Flowering is determinate with one primary flower at the end of a long (18 cm) pedicel on open flowers. Each pedicel had approximately 4 leaflets on the proximal end of the pedicel. A secondary flower arises from the base of the primary pedicel.

B. *Natural flowering season.*—Flowering occurs primarily February through October in the northern hemisphere. Initiation occurs after a cool temperature vernalization (10°–17° C.). Floriferousness may wane during hot summer days in temperate climates. Plants are initially potted using rooted cuttings, pinched two weeks later, then maintained at temperatures of 10°–12° C. for four weeks and thereafter grown for six weeks at a temperature of 18° C., for a total of 12 weeks to flower.

C. *Flower buds.*—Flower buds develop successively on secondary branches, reaching a size of 1.8 cm long and 1 cm wide prior to opening.

D. *Flowers borne.*—Singularly 6.5–14 cm above the plant canopy.

E. *Quantity of flowers.*—Secondary flowers occur progressively around the primary flower so that tight buds to mature flowers are visible at the same time.

F. *Flower head.*—1. Number of florets: 17–20 ray florets and numerous disk florets, making up a flower disk approximately 1.2 cm in diameter. 2. Shape: Narrow linear florets with obtuse to acute tips and acute bases. Ray florets approximately 3.4 cm long and 0.9 cm wide. 3. Color: Ray florets are medium purple; disk florets are violet-blue. Young flowers are light purple on opening and change to medium purple at maturity. (i) Upper surface of ray florets: Alternating longitudinal stripes near R.H.S. 78B and R.H.S. 78C. (ii) Under surface of ray florets: Dark purple veins near R.H.S. 77A and the area between the veins is near R.H.S. 77C. (iii) Disk florets: Near 95A. 4. Surface: (i) Upper surface of ray florets: Glabrous. (ii) Under surface of ray florets: Glabrous but pubescent near the base. 5. *Inflorescence size: Up to* 7.8 cm in diameter.

G. *Reproductive organs.*—1. Stamens: Short stamens emerge on outermost disk florets and progress toward the center. 2. Anther: Each disk floret has 1 stamen terminating in a 5-part anther. 3. Pollen: Copious and golden yellow. 4. Stigma: Bipartite. 5. Styles: Short, approximately 2 to 3 mm long and purple. 6. Ovary: Inferior to florets and green in color.

H. *Resistance.*—1. Frost: Withstands light frost. 2. Root, stem, foliage and flower diseases: High resistance.

What is claimed is:

1. A new and distinct cultivar of Osteospermum plant named 'Cape Daisy Lusaka', as illustrated and described.

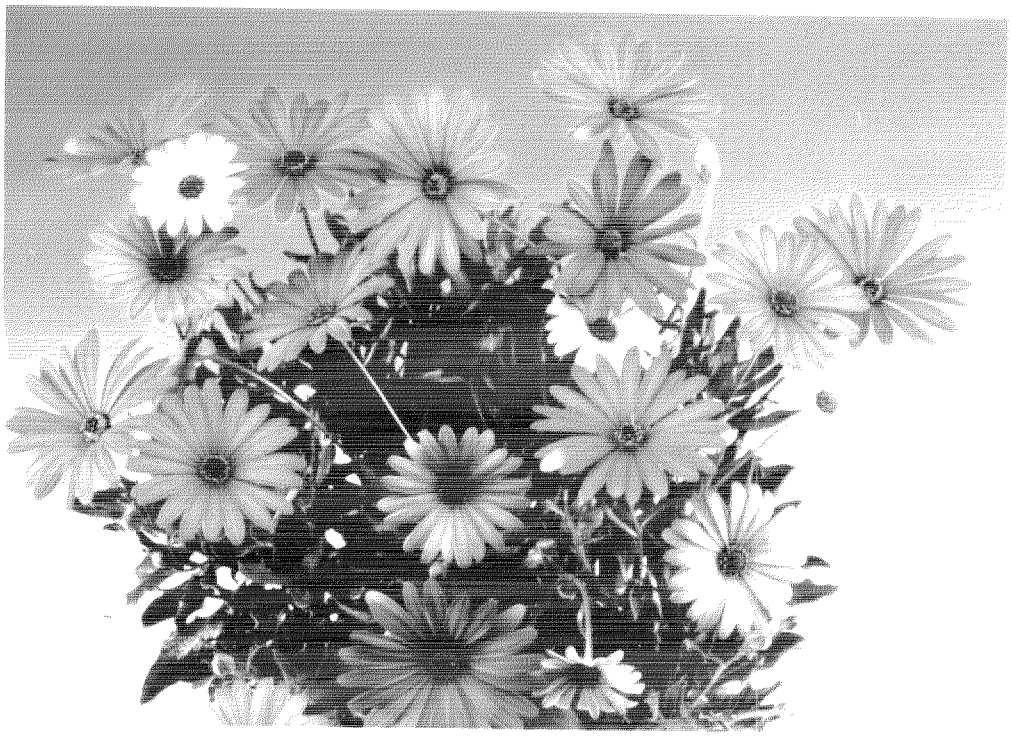

* * * * *